(12) United States Patent
Burkhardt et al.

(10) Patent No.: US 6,281,517 B1
(45) Date of Patent: Aug. 28, 2001

(54) APPARATUS FOR MONITORING PIPETTING OPERATIONS

(75) Inventors: Claudius Burkhardt, Lucerne; Fritz Gödl, Rotkreuz; Reto Seeholzer, Immensee, all of (CH)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/371,979

(22) Filed: Aug. 11, 1999

(30) Foreign Application Priority Data

Aug. 17, 1998 (CH) .................................................. 98/15395

(51) Int. Cl.$^7$ .................................................. G01N 15/06
(52) U.S. Cl. ........................ 250/573; 250/576; 356/436; 356/246
(58) Field of Search ..................... 356/436, 246, 356/414, 418; 250/573, 576, 577; 73/864.21

(56) References Cited

U.S. PATENT DOCUMENTS

| | | | |
|---|---|---|---|
| 3,999,868 | * 12/1976 | Sanz et al. | 356/246 |
| 4,410,020 | * 10/1983 | Lorenz | 73/293 |
| 4,979,821 | * 12/1990 | Schutt et al. | 356/246 |
| 5,005,434 | * 4/1991 | Watanabe et al. | 73/864.21 |
| 5,125,748 | * 6/1992 | Bjornson et al. | 356/414 |
| 5,559,339 | 9/1996 | Domanik | 250/573 |

FOREIGN PATENT DOCUMENTS

| | | |
|---|---|---|
| 42 11 003 | 10/1982 | (DE) . |
| 196 30 160 | 1/1998 | (DE) . |
| WO 97/33154 | 9/1997 | (WO) . |

OTHER PUBLICATIONS

Patent Abstract of Japan– Publication No. 05223830 A, Date of Publication Mar. 09, 1993; Method and Device for Detecting Dispensated Quantity.

Derwent Abstract of EP 819943 A, Optical system evaluating quality of fluid distribution onto test piece, e.g. medical test strip— compares results of successive illuminations of test zone to establish adequate, even spreading for correct delivery to reactive test zone, e.g. in making blood glucose measurements.

* cited by examiner

Primary Examiner—Frank G. Font
Assistant Examiner—Roy M. Punnoose
(74) Attorney, Agent, or Firm—Gibbons, Del Deo Dolan, Griffinger & Vecchione

(57) ABSTRACT

The present invention refers to an apparatus for monitoring pipetting operations, and in particular the ejection of a first liquid from a pipetting needle having a tip immersed in a second liquid. The apparatus comprises a light source that irradiates the second liquid with a light beam, and light receiver which receives the light beam emerging from the second liquid and delivers an output signal which corresponds to the received light intensity. To improve the accuracy and reliability of pipetting operations, the apparatus is provided with a light receiver adapted for continuously delivering intensity signals ($U_n$); first storage means for storing previously determined threshold values (S); second storage means for storing intensity signals ($U_n$) delivered by the light receiver and evaluation parameters ($B_m$, $A_m/A_{tot}$) derived therefrom; and at least one logic circuit for comparing the evaluation parameters ($B_m$, $A_m/A_{tot}$) with the threshold values (S) and for delivering a resulting output signal (E, F).

7 Claims, 5 Drawing Sheets

APPARATUS FOR MONITORING PIPETTING OPERATIONS

FIELD OF THE INVENTION

The present invention refers to an apparatus for monitoring pipetting operations, and in particular the ejection of a first liquid from a pipetting needle having a tip immersed in a second liquid. The apparatus comprises a light source that irradiates the second liquid with a light beam, and a light receiver which receives the light beam emerging from the second liquid and delivers an output signal which corresponds to the received light intensity.

BACKGROUND OF THE INVENTION

Light barriers comprising a light source and a light receiver, e.g. for the detection of passing objects, are generally known. Further, it is known that gas bubbles contained in a liquid column are detectable since their optical density is different from that of the liquid column. Therefore, gas bubbles in a liquid column can be detected by means of a suitable light barrier. An apparatus for this purpose is described by WO-A-97/33154.

With respect to automatic analyzers for the analysis of liquids, it is known that these liquids are handled in small quantities, e.g. in portions of minimally 1 to 2 microliters, by aspiration into and ejection out of pipetting needles. In the analysis process, the appearance of bubbles in the needles constitutes an important source of errors since such bubbles can strongly influence the quantities of the ejected liquids.

SUMMARY OF THE INVENTION

The main aim of the invention is therefore to provide an apparatus which allows for the monitoring of the aspiration and ejection of a liquid into and out of a pipetting needle with high accuracy in order to prevent analysis errors. A further aim of the invention is that this monitoring is obtained by an optical arrangement.

According to the invention, these aims are attained by an apparatus comprising:

- a light source having a light beam to irradiate the second liquid;
- a light receiver for receiving the light beam emerging from the second liquid wherein said light receiver is adapted for continuously delivering intensity signals;
- an output signal emitted by the light receiver corresponding to the received light intensity,
- first storage means for storing previously determined threshold values;
- second storage means for storing the intensity signals delivered by the light receiver and evaluation parameters derived therefrom; and
- at least one logic circuit for comparing said evaluation parameters with said threshold values and for delivering a resulting output signal.

The present invention allows measurements in automatic analyzers which are substantially more reliable, thereby considerably improving the information content and usefulness of such measurements.

DETAILED DESCRIPTION OF THE INVENTION

Figure 1:
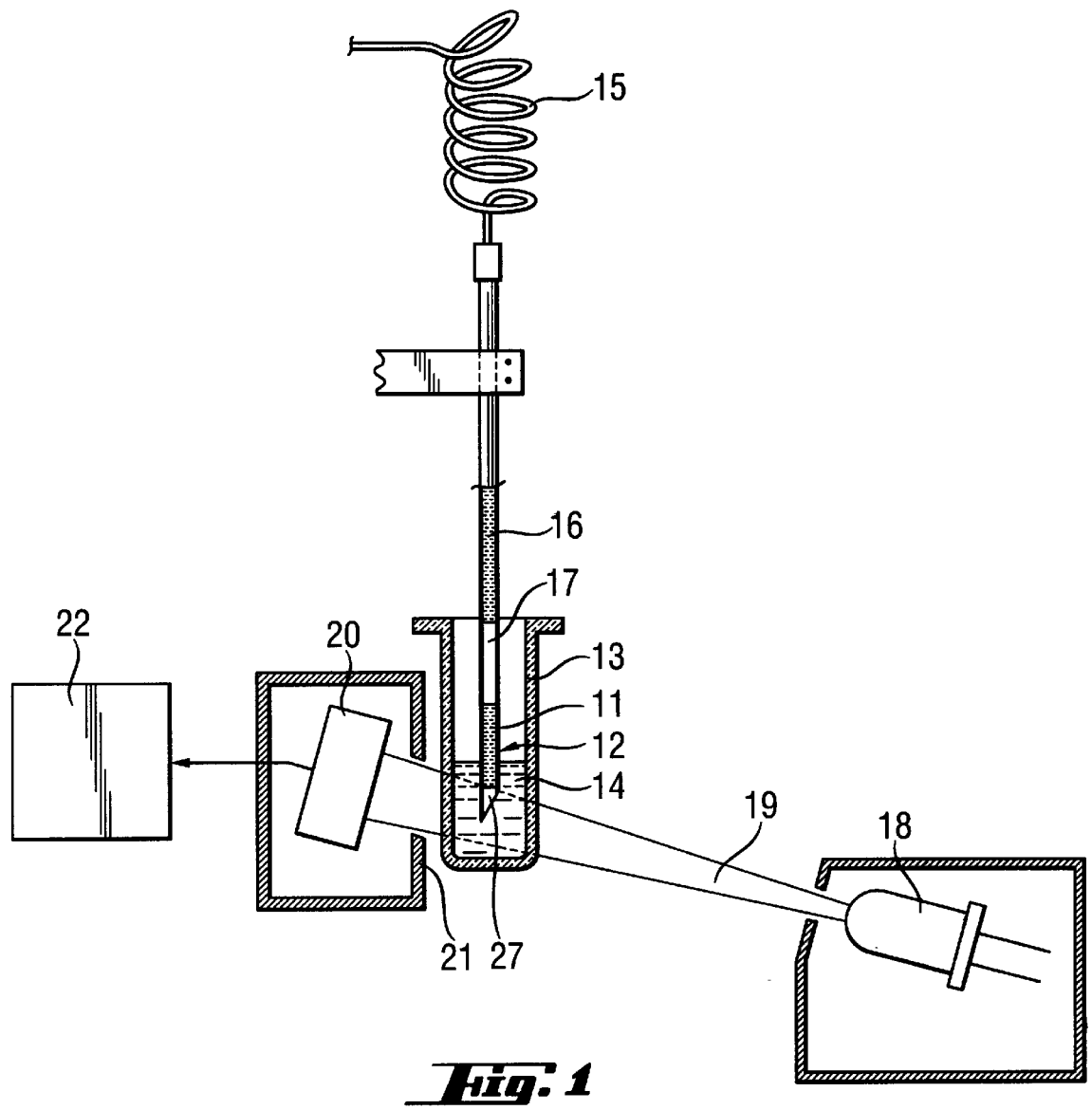
FIG. 1 illustrates the apparatus according to the invention.

As shown in FIG. 1, a pipetting needle 12 contains a first liquid 11 which is to be ejected. Needle 12 is inserted into a vessel 13 while its tip is immersed in a second liquid 14, different from first liquid 11. The ejected liquid 11 is intended to be mixed with second liquid 14. Pipetting needle 12 is connected to a flexible tube 15 which allows control of aspiration and ejection, respectively, of liquid 11 by means of pressure variations. Pipetting needle 12 ejects a quantity, the minimal volume of which is preferably approximately one microliter, of sample liquid 11.

Above the first liquid 11 having a volume that is defined, a flexible tube 15 contains a separating bubble 17 which separates the first liquid 11 from a third, auxiliary liquid 16 that constantly remains in the upper part of pipetting needle 12 to exert hydraulic pressure. The tip of needle 12 contains a protecting bubble 27 which extends up to the first liquid 11 and forms a closure which separates the interior of pipetting needle 12 from the exterior and prevents an involuntary ejection of a portion of first liquid 11.

The apparatus shown in FIG. 1 comprises a light source 18, e.g. a LED (light emitting diode) emitting a light beam 19 in proximity of the infrared range (e.g. at a wavelength of about 900 nm) and an associated light receiver 20. The latter is connected to electronic detector circuitry 22. Light beam 19 passes through vessel 13 and liquid 14 contained therein in the form of a relatively large and oblique beam, so that total reflection on the bubble walls causes large variations of light intensity received by light receiver 20. In order to eliminate any interfering background radiation, light receiver 20 is externally shielded by a screen 21. In this manner, even the smallest individual bubbles ejected into second liquid 14 by needle 11 can be detected while they are slowly ascending.

Figure 2:
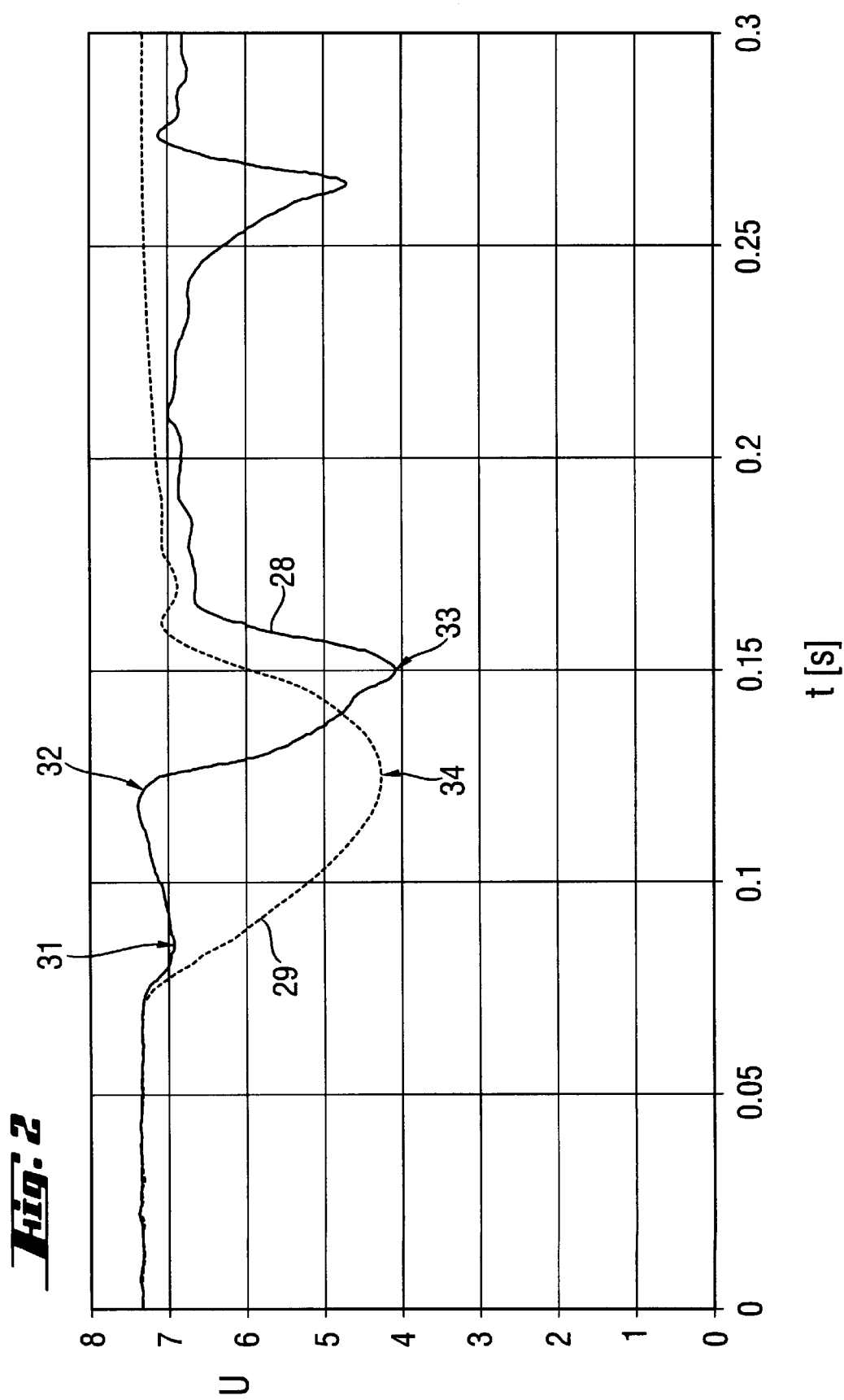
FIG. 2 is a graph of characteristic intensity versus time diagrams.

The graph shown in FIG. 2 depicts a typical behavior of output signal/intensity signal U provided by light receiver 20 as a function of time t for two different scenarios. In the normal scenario, the required amount of first liquid 11 is free of bubbles when it is contained in pipetting needle 12. Solid line 28 shows a typical course of output signal U in this scenario.

As shown in FIG. 2, after the beginning of the ejecting procedure a first local minimum 31 of small depth appears which corresponds to the ejection of protecting bubble 27. The following local maximum 32 corresponds to the ejection of first liquid 11. As soon as the liquid 11 is completely emitted from pipetting needle 12, a part of separating bubble 17 follows which causes a second, deeper minimum 33.

Broken line 29 shown in FIG. 2 is a typical behavior of output signal U in a second scenario in which little or no liquid 11, e.g. mainly air, from pipetting needle 12 is introduced into second liquid 14. In this scenario, a single minimum 34 appears whose depth is about the same as that of minimum 33 in the first scenario. In practice, the curve U versus T can have a great variety of shapes each of which corresponds to a variety of the shapes of curves 28 and 29 represented in FIG. 2.

Figure 3:
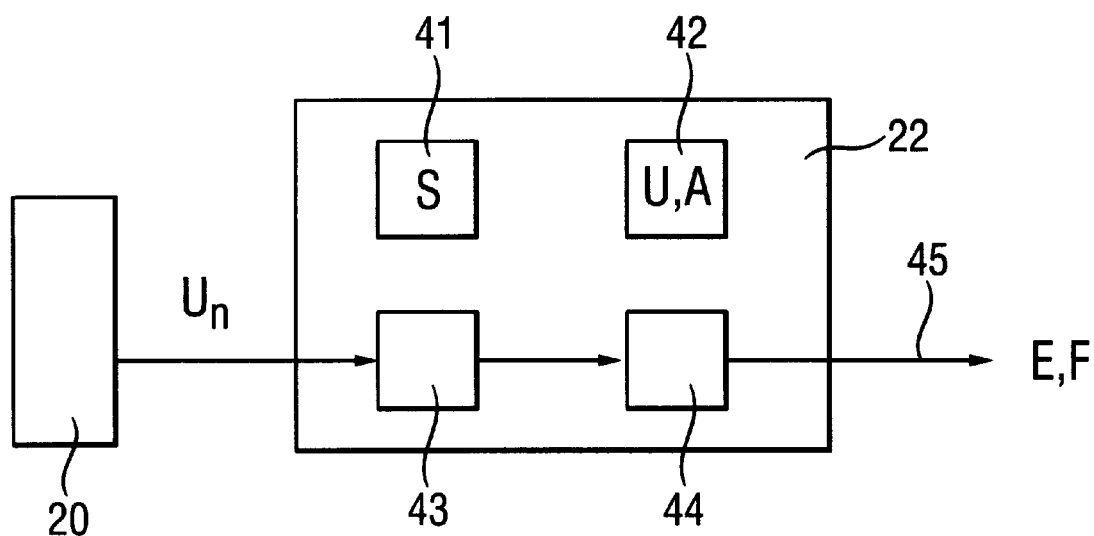
FIG. 3 is a block diagram of the electronic circuitry connected to a light receiver.

FIG. 3 illustrates a block diagram of detection circuit 22. This circuit 22 comprises first storage means 41 and second storage means 42 as well as two logic circuits 43 and 44. Detection circuit 22 receives measured signals $U_n$ from light receiver 20 and it outputs control signals E and F, respectively, on line 45.

In storage means 41, reference values are stored which correspond to the typical intensity versus time graph shown in FIG. 2. These reference values serve as preferable threshold values S. In storage means 42, intensity values, i.e. measured values $U_n$ (n: continuous numbering) detected in the course of ejecting liquid 11 from pipetting needle 12, are continuously stored so that a sequence of measured values is always available for processing. In order to reduce the problematic effect of statistical variations, the measured values $U_n$ stored in storage means 42 are preferably filtered measured values. For example, the filtering operation can be achieved by averaging five successive individual values.

First logic circuit 43 continuously determines difference values ($dU_n$) such that $dU_n = U_n - U_{n-1}$ from successive (preferably filtered) measured values $U_n$. The quotient of these difference values and a time interval dt, i.e. $dU_n/dt$, corresponds to the respective slopes of the curves represented in FIG. 2. These slopes, and in particular their average value and their location in time, allow important deductions. Furthermore, the sequence of difference values $dU_n$ also allows the determination of the minima and/or maxima of the respective intensity versus time graph. The intensity values allow the determination of the associated intensities at extreme points (maximum or minimum points).

Figure 4:
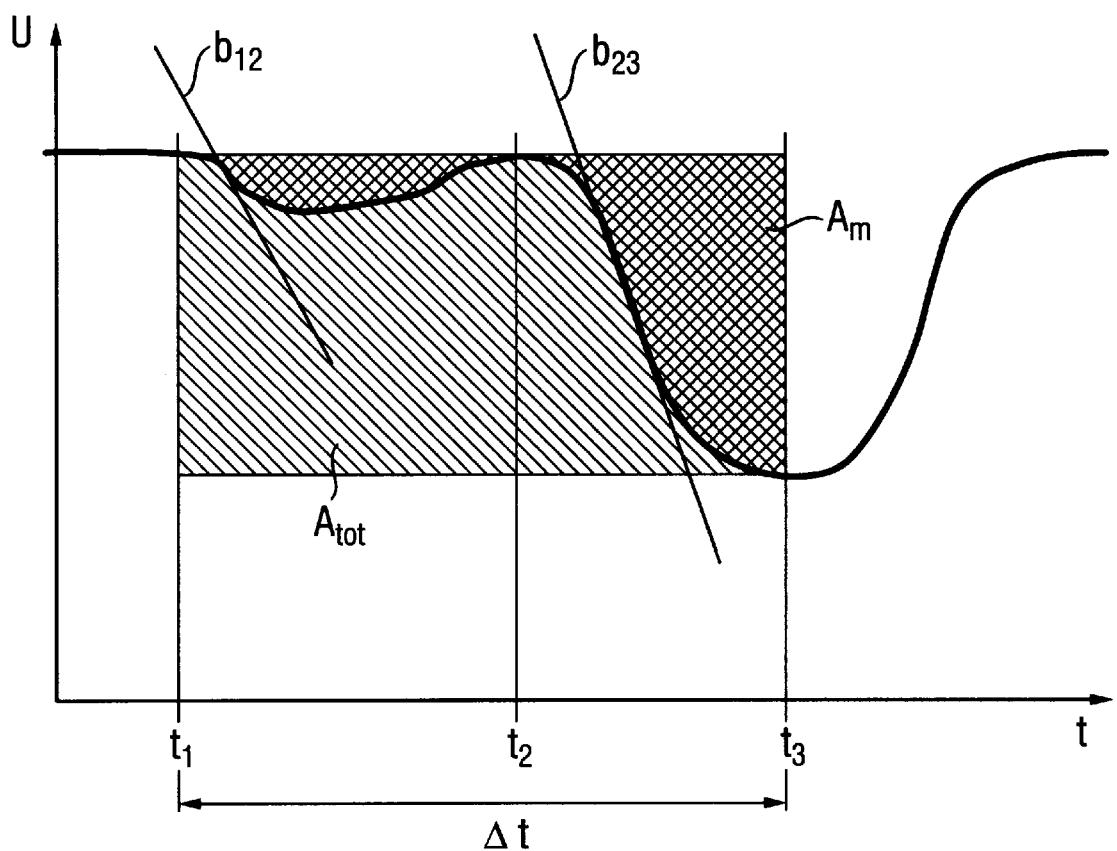
FIG. 4 is a graph of intensity integrals.

For example, the graph shown in FIG. 4 illustrates the slope $b_{12} = (dU/dt)$ related to the minimum between $t_1$ and $t_2$. The slopes related to extreme points constitute first evaluation parameters $B_m$ (where m=1, 2, 3, etc.) In a preferred embodiment, intensity values at extreme points are also used as evaluation parameters $B_m$.

Integrals $A_{tot}$ and Am are used in order to obtain further evaluation parameters. Surfaces defined by the intensity versus time graphs according to FIG. 2 are determined. Using this procedure, a graph as shown in FIG. 4 is derived which corresponds to that of FIG. 2. Integral $A_m$ corresponds to the surface above the respective curve, starting at time $t_1$ and ending at time $t_3$. The integral $A_{tot}$ corresponds to the associated rectangular surface defined by $t_1$ and the time $\Delta t$. The ratio $A_m/A_{tot}$ of these respective integrals constitutes an additional evaluation parameter.

In second logic circuit 44 shown in FIG. 3, the respective evaluation parameters are compared to the threshold values available in first storage means 41. As soon as the criteria described below are fulfilled, logic circuit 44 emits on line 45 either an end signal E or an error signal F. In a preferred embodiment, logic circuits 43 and 44 and storage means 41 and 42 are configured so that they are capable of performing a null point adjustment.

Detection circuit 22 may be composed of individual circuits in a conventional manner, e.g. using operational amplifiers. In a preferred embodiment, detection circuit 22 is a program-controlled processor which includes associated storage means where logic circuits 43 and 44 serially perform program routines.

Figure 5:
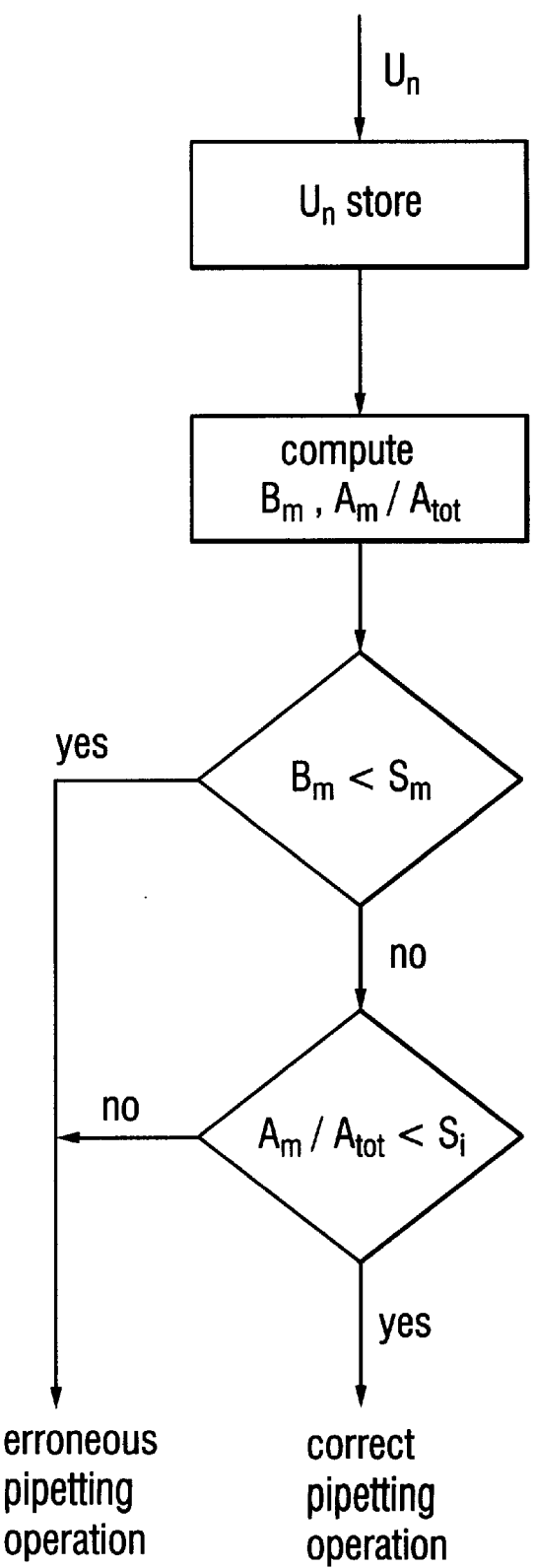
FIG. 5 is a flow diagram illustrating the functionality of a detection circuit.

FIG. 5 is a flow diagram which illustrates the functionality of detection circuit 22 shown in FIG. 3. Intensity values $U_m$ delivered by light receiver 20 are stored in the form of raw data in storage means 42. In initial processing steps, storage means 42 compute the above-mentioned evaluation parameters $B_m$ and $A_m/A_{tot}$. Subsequently, an assessment is performed to determine whether the first evaluation parameters $B_m$ correspond to the conditions defined by the stored threshold values S and whether the ratio of integrals $A_m/A_{tot}$ does not exceed another threshold value $S_i$. If the assessment indicates faultless pipetting, a positive end signal E is emitted. Otherwise, an error may have occurred and an error signal F is emitted. This error signal either triggers a stop signal or the repetition of the pipetting procedure.

In a preferred embodiment of the present invention, it is understood that the threshold values S are previously determined with comparable samples. Furthermore, a null point adjustment is necessary at least after every initialization. This allows for the elimination or minimization of disturbing factors such as differences in volume of second liquid 14 and differences in transparency, refraction index and viscosity of liquids 11 and 14 and of vessel 13.

An advantage of the present invention is the evaluation of a large series of measured values using slopes $dU_n/dt$ and integrals A. The capability of detecting possible errors is thereby considerably increased.

To those skilled in the art, numerous alternative embodiments of light source 18, light receiver 20 and processing of the signals by detection circuit 22 are possible within the scope of the described invention. Such alternatives may concern the geometry, the light wavelength, the choice and detection of the data to be compared, the basic flow diagram, etc.

Numerous modifications and alternative embodiments of the invention will be apparent to those skilled in the art in view of the foregoing description. Accordingly, this description is to be construed as illustrative only and is for the purpose of teaching those skilled in the art the best mode of carrying out the invention. Details of the apparatus may be varied substantially without departing from the spirit of the invention and the exclusive use of all modifications which come within the scope of the appended claims is reserved.

What is claimed is:

1. An apparatus for monitoring pipetting of a first liquid from a pipetting needle having a tip immersed in a second liquid, said apparatus comprising:

a light source having a light beam to irradiate the second liquid;

a light receiver for receiving the light beam emerging from the second liquid wherein said light receiver is adapted for continuously delivering intensity signals ($U_n$);

an output signal emitted by the light receiver corresponding to the received light intensity, first storage means for storing previously determined threshold values (S);

second storage means for storing the intensity signals ($U_n$) delivered by the light receiver and evaluation parameters ($B_m$ and $A_m/A_{tot}$) derived therefrom; and at least one logic circuit for comparing said evaluation parameters ($B_m$ and $A_m/A_{tot}$) with said threshold values (S) and for delivering a resulting output signal (E and F).

2. The apparatus of claim 1, wherein first ones of said derived evaluation parameters ($B_m$) are curve slopes in the intensity versus time graph, and wherein second ones of said derived evaluation parameters $A_m/A_{tot}$ are the quotients of two integrals corresponding to two surfaces of the intensity versus time graph defined by a starting time ($t_1$) and a time interval ($\Delta t$).

3. The apparatus of claim 2, wherein the intensity values at extreme points are included in said derived evaluation parameters ($B_m$).

4. The apparatus of claim 1, wherein the measured values ($U_n$) of the intensity signals stored in said second storage means are average values.

5. The apparatus of claim 1, wherein said logic circuits and said storage means are part of a program controlled processor.

6. The apparatus of claim 1, wherein said logic circuits and said storage means are capable of performing a null point adjustment.

7. The apparatus of claim 1, wherein the minimal volume of the ejected first liquid is approximately 1 microliter.

* * * * *